(12) United States Patent
Carroll et al.

(10) Patent No.: US 12,036,366 B2
(45) Date of Patent: Jul. 16, 2024

(54) DEVICE AND METHOD FOR TREATING HYPOXIA

(71) Applicant: Duke University, Durham, NC (US)

(72) Inventors: Kathleen Carroll, Durham, NC (US); Lindsay Boole, Durham, NC (US); Loretta Que, Durham, NC (US)

(73) Assignee: Duke University, Durham, NC (US)

( * ) Notice: Subject to any disclaimer, the term of this patent is extended or adjusted under 35 U.S.C. 154(b) by 550 days.

(21) Appl. No.: 17/320,647

(22) Filed: May 14, 2021

(65) Prior Publication Data
US 2021/0353889 A1 Nov. 18, 2021

Related U.S. Application Data

(60) Provisional application No. 63/025,245, filed on May 15, 2020.

(51) Int. Cl.
| | | |
|---|---|---|
| *A61M 16/06* | (2006.01) | |
| *A61M 16/10* | (2006.01) | |
| *A61M 16/20* | (2006.01) | |
| *A63B 23/18* | (2006.01) | |

(52) U.S. Cl.
CPC ........ *A61M 16/06* (2013.01); *A61M 16/1005* (2014.02); *A61M 16/1055* (2013.01); *A61M 16/1065* (2014.02); *A61M 16/201* (2014.02); *A61M 16/107* (2014.02); *A61M 16/20* (2013.01); *A61M 16/208* (2013.01); *A61M 2202/0208* (2013.01); *A61M 2205/586* (2013.01); *A61M 2230/205* (2013.01); *A63B 23/18* (2013.01)

(58) Field of Classification Search
CPC .............. A61M 16/06; A61M 16/0605; A61M 16/0616; A61M 16/1005; A61M 16/1055; A61M 16/1065; A61M 16/107; A61M 16/20; A61M 16/201; A61M 16/208; A61M 2202/0208; A61M 2205/586; A61M 15/0086; A63B 23/18
See application file for complete search history.

(56) References Cited

U.S. PATENT DOCUMENTS

| | | | |
|---|---|---|---|
| 4,316,458 A | * | 2/1982 | Hammerton-Fraser ..................... A61M 16/20 128/205.24 |
| 4,823,828 A | | 4/1989 | McGinnis |
| 5,598,839 A | | 2/1997 | Niles et al. |
| 7,059,324 B2 | | 6/2006 | Pelerossi et al. |
| 7,806,120 B2 | | 10/2010 | Loomas |
| 8,469,031 B2 | | 6/2013 | Winter et al. |
| 8,656,915 B2 | | 2/2014 | Bayron et al. |
| 2003/0140925 A1 | | 7/2003 | Sapienza et al. |
| 2006/0249158 A1 | * | 11/2006 | Dhuper ............. A61M 15/0088 128/206.28 |
| 2010/0095965 A1 | * | 4/2010 | Piper ................. A61M 16/0816 128/205.24 |
| 2016/0256661 A1 | * | 9/2016 | Battersby .......... A61M 16/1045 |
| 2017/0136205 A1 | * | 5/2017 | Rusher ................ A61M 16/208 |
| 2019/0117925 A1 | * | 4/2019 | Boole ............... A61M 16/0605 |

* cited by examiner

*Primary Examiner* — Joseph D. Boecker
(74) *Attorney, Agent, or Firm* — Casimir Jones, S.C.; Brian F. Bradley (57) ABSTRACT

A device is disclosed herein and includes a facemask, an outlet valve in fluid communication with the facemask, a grip positioned between the facemask and the outlet valve, and an inlet valve in fluid communication with the facemask. The inlet valve is positioned within the grip. The device is used in a method for treating hypoxia in a subject.

20 Claims, 7 Drawing Sheets

DEVICE AND METHOD FOR TREATING HYPOXIA

CROSS-REFERENCE TO RELATED APPLICATIONS

This application claims priority to U.S. Provisional Patent No. 63/025,245 filed on May 15, 2020, the entire contents of which are incorporated herein by reference.

BACKGROUND

Oxygen deficiency in humans can be caused by a variety of reasons and can likewise be treated through a variety of methods. For some cases, a treatment regimen can include maintaining an elevated air pressure in the lungs via a bag-valve-mask or other noninvasive (e.g., CPAP) or invasive mechanical ventilator. However, conventional portable devices tend to be awkward to use, do not protect against the spread of infection, require a power source or a charged battery, and require a headgear to hold the device over the patient's mouth and nose. Also, the inflow valve on a conventional portable breathing treatment system is often at least partially blocked by the grasp of a user. Thus, there is an ongoing need to address these, and other challenges, associated with portable devices for treating hypoxia.

SUMMARY

The summary is provided to introduce a selection of concepts that are further described below in the detailed description. This summary is not intended to identify key or essential features of the claimed subject matter, nor is it intended to be used as an aid in limiting the scope of the claimed subject matter.

The disclosure provides, in one aspect, a device including a facemask, an outlet valve in fluid communication with the facemask, a grip positioned between the facemask and the outlet valve, and an inlet valve in fluid communication with the facemask. The inlet valve is positioned within the grip.

In some embodiments, a first airflow path is defined through the inlet valve when the device is in a first configuration, and a second airflow path is defined through the outlet valve when the device is in a second configuration.

In some embodiments, the first airflow path is to the facemask and wherein the second airflow path is from the facemask.

In some embodiments, an air inlet is formed between the grip and the facemask.

In some embodiments, the air inlet is an opening positioned between an axial end of the grip and the facemask.

In some embodiments, the opening circumferentially extends 360 degrees.

In some embodiments, a cavity formed in the grip is in fluid communication with the opening.

In some embodiments, an oxygen delivery device is fluidly coupled to the air inlet.

In some embodiments, the device further includes a seat coupled to the grip, wherein the inlet valve is coupled to the seat.

In some embodiments, the seat is in fluid communication with an air inlet formed between the grip and the facemask, and wherein the seat includes an aperture at least partially covered by the inlet valve.

In some embodiments, the inlet valve is an umbrella valve with a stem at least partially received within a hub formed in the seat.

In some embodiments, the outlet valve is a positive end expiration pressure valve.

In some embodiments, the device further includes a filter in fluid communication with the facemask.

In some embodiments, the filter is positioned within a filter housing with a first end coupled to the grip and a second end coupled to the outlet valve.

In some embodiments, a method of treating hypoxia in a subject includes the device.

The disclosure provides, in another aspect, a method of treating hypoxia in a subject. The method includes providing a device including a valve to the subject, measuring a first oxygen saturation of the subject, adjusting the valve to a first setting corresponding to a first pressure threshold, and instructing the subject to inhale and exhale through the device. The method further includes measuring a second oxygen saturation of the subject, adjusting the valve to a second setting corresponding to a second pressure threshold, the second pressure threshold is larger than the first pressure threshold. The method further includes instructing the subject to inhale and exhale through the device and measuring a third oxygen saturation of the subject.

In some embodiments, the method includes determining a peak oxygen saturation, wherein the peak oxygen saturation is the largest of the first oxygen saturation, the second oxygen saturation, and the third oxygen saturation; determining a treatment setting of the valve corresponding to the peak oxygen saturation; and adjusting the valve to the treatment setting.

In some embodiments, the method includes waiting at least 30 seconds between measurements of the oxygen saturation of the subject.

In some embodiments, the subject has been diagnosed with COVID-19.

In some embodiments, the method includes decontaminating the device by at least one of removing the valve and wiping down the device.

Other aspects of the disclosure will become apparent by consideration of the detailed description and accompanying drawings.

BRIEF DESCRIPTION OF THE DRAWINGS

The accompanying figures and examples are provided by way of illustration and not by way of limitation. The foregoing aspects and other features of the disclosure are explained in the following description, taken in connection with the accompanying example figures (also "FIG.") relating to one or more embodiments.

Before any embodiments are explained in detail, it is to be understood that the invention is not limited in its application to the details of construction and the arrangement of components set forth in the following description or illustrated in the following drawings. The invention is capable of other embodiments and of being practices or of being carried out in various ways.

DETAILED DESCRIPTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that an apparatus comprises components A, B, and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human who is undergoing hypoxia treatment with a device as described herein.

Unless otherwise defined, all technical terms used herein have the same meaning as commonly understood by one of ordinary skill in the art to which this disclosure belongs.

Figure 1:
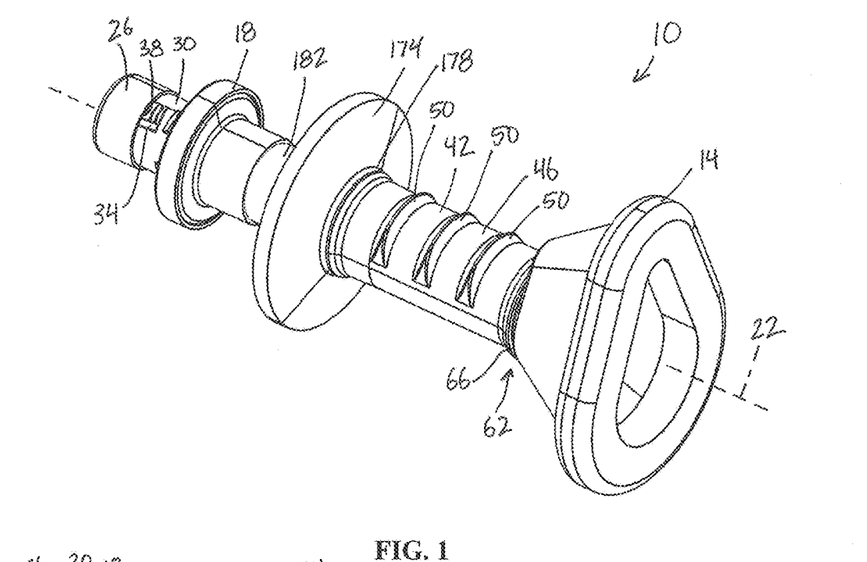
FIG. 1 is a perspective view of a device for the treatment of, among other things, hypoxia in a subject.

With reference to FIG. 1, a device 10 includes a facemask 14 and an outlet valve 18 in fluid communication with the facemask 14. In the illustrated embodiment, the outlet valve 18 is positioned axially aligned with the facemask 14 along a longitudinal axis 22. In other words, the longitudinal axis 22 intersects both the outlet valve 18 and the facemask 14. The device 10 is a low-cost, non-invasive, and portable hypoxia device that can be used to improve oxygenation in a subject. The device 10 decreases the respiratory muscle work of breathing, decreases atelectasis, and increases functional residual capacity. Specifically, the outlet valve 18 creates a positive pressure within a subject that reduces atelectasis and recruits alveoli to reduce ventilation-perfusion mismatch. In some embodiments, the device 10 is a single use device. In some embodiments, the facemask 14 is a customized face mask. In some embodiments, the facemask covers both the mouth and nose of the user.

The outlet valve 18 is any suitable type of pressure valve. In some embodiments, the outlet valve 18 is a positive end expiration pressure valve (i.e., a PEEP valve). The outlet valve 18 maintains a threshold pressure within the device 10. In other words, the outlet valve 18 maintains a positive pressure in the facemask 14 and correspondingly within the subject. In some embodiments, the outlet valve 18 is adjustable to different pressure thresholds. For example, the outlet valve 18 can be adjusted with an adjustable orifice size or by spring actuation. In some embodiments, the adjustment is in a continuous range of pressure threshold values (e.g., any pressure value between approximately 0 and approximately 20 cm $H_2O$). In other embodiments, the adjustment is within a discrete range of pressure threshold values (e.g., 5 cm $H_2O$, 10 cm $H_2O$, 15 cm $H_2O$, and 20 cm $H_2O$). In some embodiment, the outlet valve 18 is adjustable to a pressure threshold within a range of approximately 1 cm $H_2O$ to approximately 150 cm $H_2O$. In some embodiments, the adjustment of the outlet valve 18 is tool-free (i.e., does not require any tools).

With reference to FIG. 1, in the illustrated embodiment, the outlet valve 18 includes a knob 26 that is adjusted by hand relative to a stem 30 between different pressure thresholds. In some embodiments, the knob 26 linearly translates along the longitudinal axis 22 as the knob 26 is rotated relative to the stem 30. Indicia 34 are positioned on the stem 30 of the outlet valve 18 to indicate to a user the pressure threshold setting of the outlet valve 18. For example, in the illustrated embodiment, a bottom surface 38 of the knob 26 aligns with the indica 34 corresponding to the pressure setting. In some embodiments, the indicia 34 includes lines, number, and/or gradations corresponding to the 5, 10, 15, and 20 cm $H_2O$ pressure threshold settings of the outlet valve 18.

Figure 2:
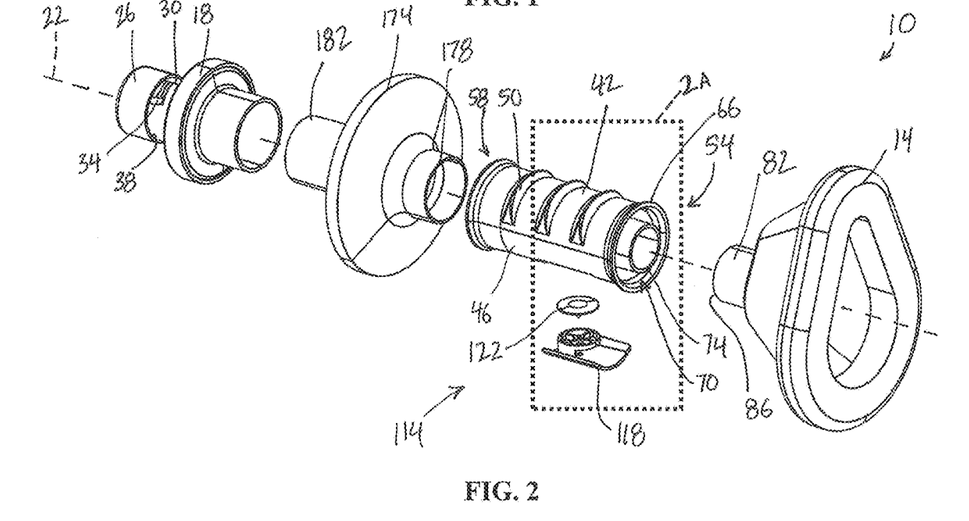
FIG. 2 is an exploded view of the device of FIG. 1.

With continued reference to FIGS. 1 and 2, the device 10 includes a grip 42 positioned between the facemask 14 and the outlet valve 18. In the illustrated embodiment, the grip 42 includes an outer cylindrical surface 46 with a plurality of ribs 50 formed on the outer cylindrical surface 46. The grip 42 includes a first axial end 54 fluidly coupled to the facemask 14 and a second axial end 58, positioned opposite the first axial end 54, fluidly coupled to the outlet valve 18. In the illustrated embodiment, the grip 42 is oriented such that the outer cylindrical surface 46 extends along the longitudinal axis 22. As explained in greater detail herein, the device 10 is grasped by a subject at the grip 42 and the facemask 14 is firmly pressed around the nose and mouth of the subject.

Figure 5:
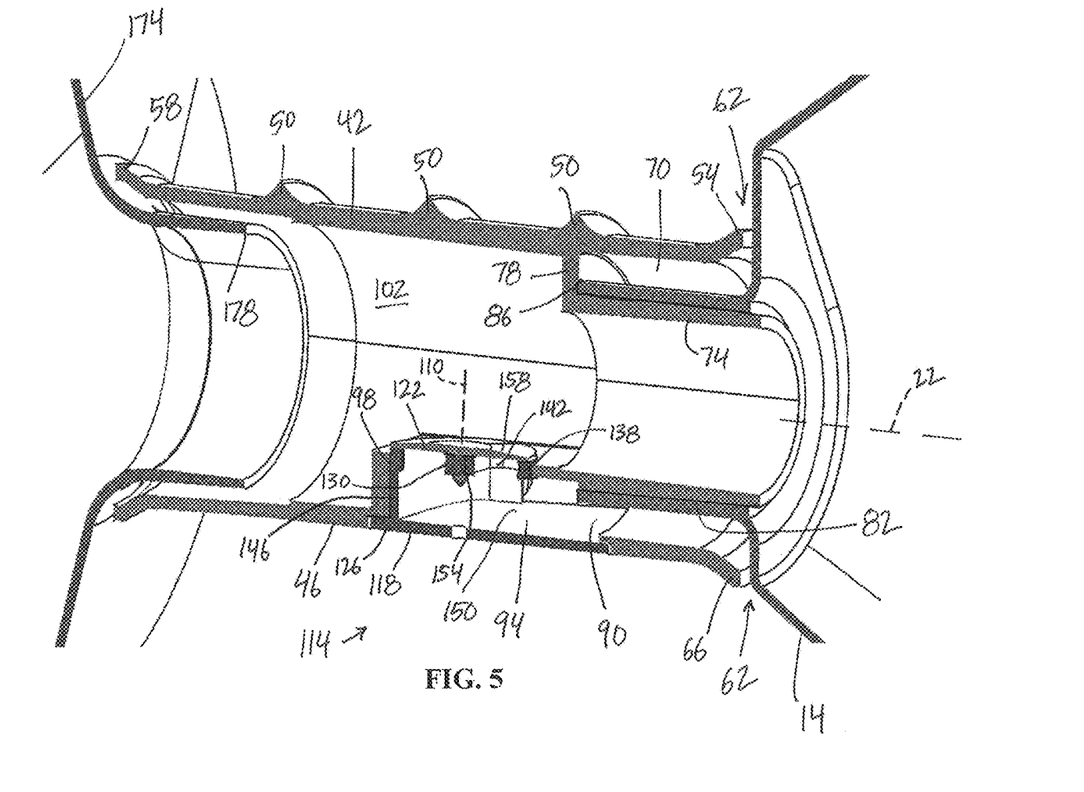
FIG. 5 is a perspective partial tear-away view of the device of FIG. 1.

With reference to FIG. 5, an air inlet 62 is formed between the grip 42 and the facemask 14. In some embodiments, the air inlet 62 is an opening positioned between the first axial end 54 of the grip 42 and the facemask 14. In some embodiments, the opening circumferentially extends at least approximately 90 degrees. In other embodiments, the opening circumferentially extends at least approximately 180 degrees. In the illustrated embodiment, the opening extends 360 degrees. In the illustrated embodiment, the first axial end 54 of the grip 42 includes a skirt portion 66 that flares radially away from the longitudinal axis 22. As explained in greater detail herein, the air inlet 62 is configured such that it is not blocked or obstructed during use of the device 10 by a subject.

With continued reference to FIG. 5, the air inlet 62 is in fluid communication with a cavity 70 formed in the grip 42. In the illustrated embodiment, the cavity 70 extends circumferentially around a mounting boss 74 formed on the grip 42. A wall portion 78 extends radially inward from the outer cylindrical surface 46 to the mounting boss 74. In the illustrated embodiment, the cavity 70 is at least partially formed by the wall portion 78 and the mounting boss 74. In some embodiments, the cavity 70 is annular. In the illustrated embodiment, the cavity 70 extends entirely (e.g., 360 degrees) around the mounting boss 74.

With continued reference to FIG. 5, the facemask 14 includes a stem 82 that corresponds to and is removable from the mounting boss 74 of the grip 42. The stem 82 is coupled to the mounting boss 74 with a tool-less fit (e.g., a press fit, a snap fit, a twist lock, etc.). In other words, the user is able to attach and remove the facemask 14 from the first axial end 54 of the grip 42 without the use of a tool. In the illustrated embodiment, the stem 82 mounts around the mounting boss 74. In some embodiments, an axial end 86 of the stem 82 abuts the wall portion 78 to maintain a minimum distance for the air inlet 62. In other words, the wall portion 78 prevents a user from closing the air inlet 62 when assembling the facemask 14 to the grip 42, thereby simplifying assembly of the device 10.

Figure 3:
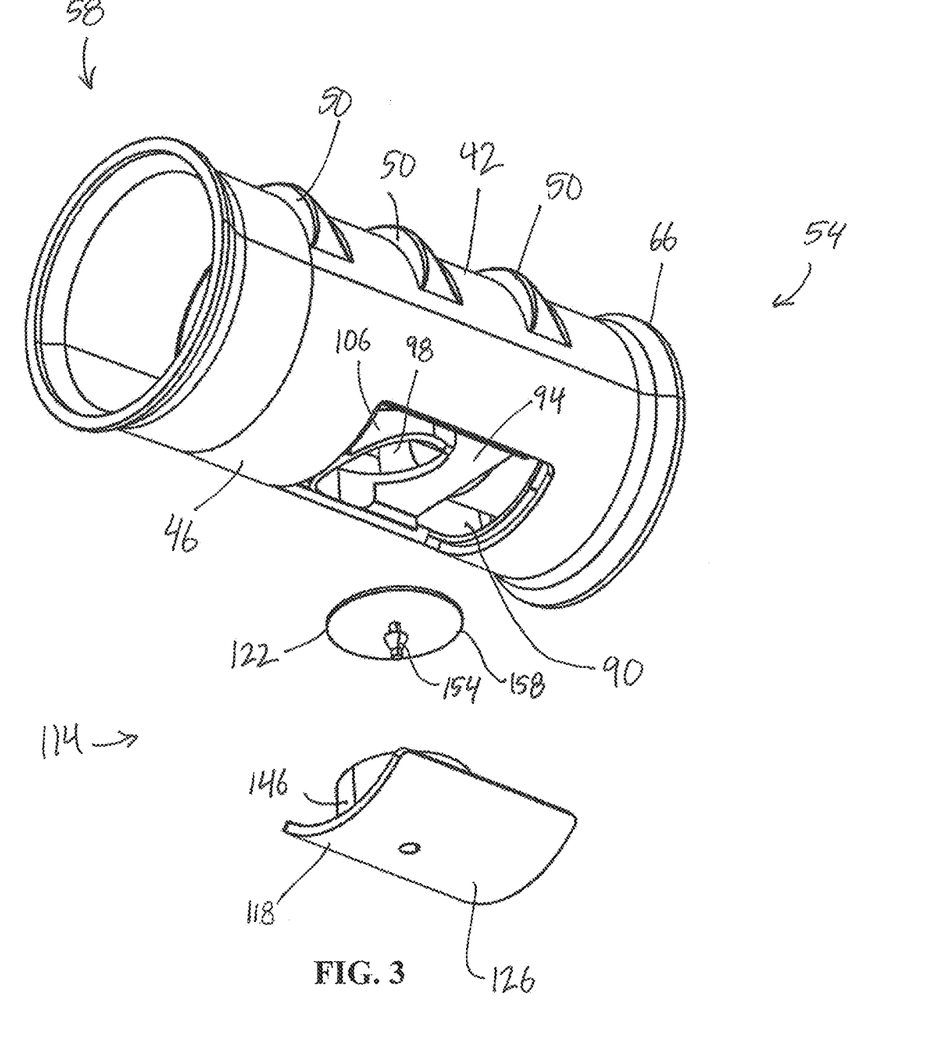
FIG. 3 is an exploded view of a grip, a seat, and an inlet valve of the device of FIG. 1.

With reference FIG. 3, the wall portion 78 of the cavity 70 includes an opening 90 that places the cavity 70 in fluid communication with a channel 94 at least partially formed in the grip 42. The channel 94 in the grip 42 further includes an aperture 98 that places the channel 94 in fluid communication with a central chamber 102 (i.e., a central passageway) of the grip 42. In the illustrated embodiment, the aperture 98 is circular with an arcuate guide 106 extending therefrom. In the illustrated embodiment, the aperture 98 defines an axis 110 that is orthogonal to the longitudinal axis 22. In the illustrated embodiment, the central chamber 102 extends along the longitudinal axis 22.

Figure 2A:
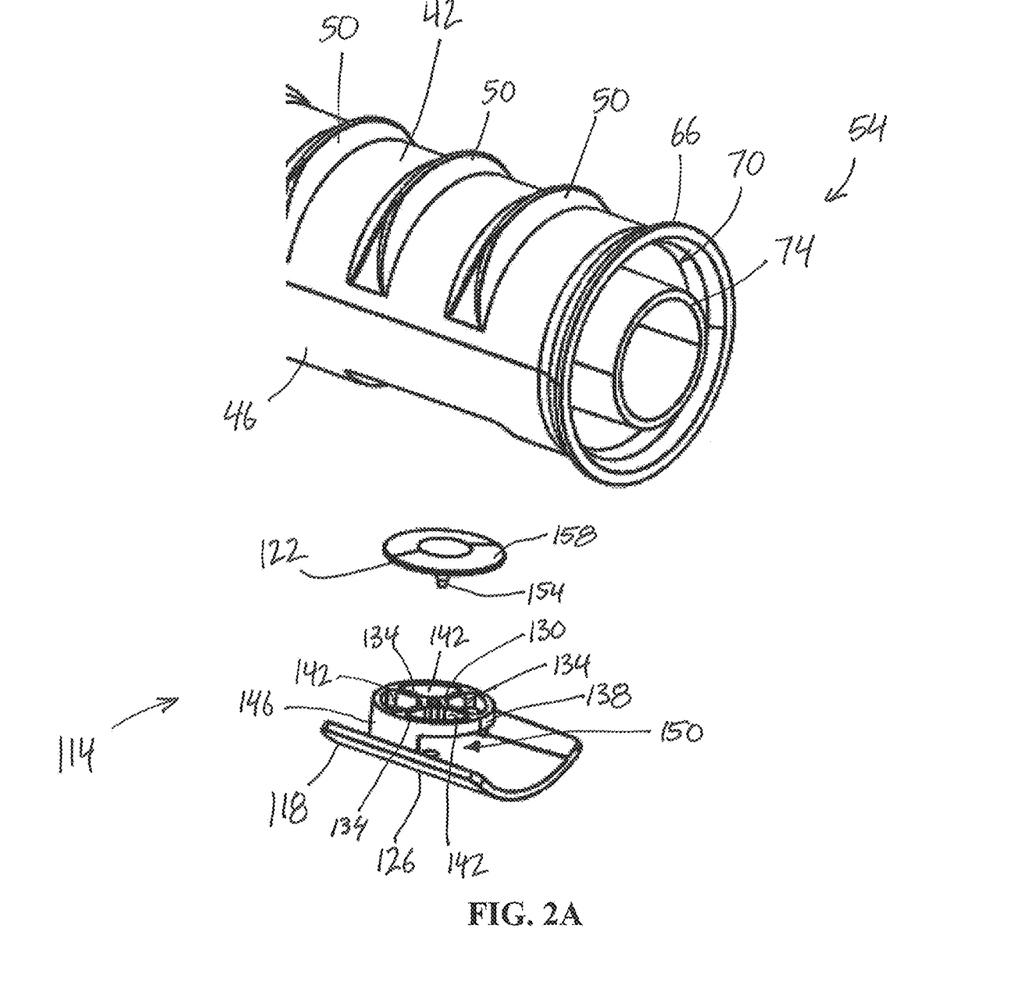
FIG. 2A is an enlarged view of a portion of FIG. 2.

With reference to FIGS. 2A and 3, the device 10 includes an inlet valve assembly 114 with a seat 118 and an inlet valve 122. The inlet valve assembly 144 is coupled to the grip 42. In the illustrated embodiment, the inlet valve 122 is coupled to the seat 118 and both are positioned within the grip 118 when the seat 118 is assembled to the grip 42. In the illustrated embodiment, the inlet valve 122 is shrouded by the seat 118. The seat 118 includes an outer wall 126 (FIG. 3) that is cylindrically shaped and when the seat 118 is coupled to the grip 42, the outer wall 126 is flush or substantially flush with the outer cylindrical surface 46 of the grip 42. In the illustrated embodiment, the outer wall 126 at least partially encloses the airflow channel 94. In other words, the channel 94 is at least partially formed by the grip 42 and the seat 118 (FIG. 5). Specifically, the seat 118 is in fluid communication with the air inlet 62 by fluid communication with the opening 90.

With continued reference to FIG. 2A, the seat 118 includes a hub 130, spokes 134 radially extending from the hub 130, and outer rim 138 coupled to the spokes 134. A plurality of apertures 142 are formed between adjacent spokes 134. The hub 130, the spokes 134, the outer rim 138, and the plurality of apertures 142 are spaced from the outer wall 126 by a wall portion 146 that extends between the outer wall 126 and the outer rim 138. In the illustrated embodiment, the wall portion 146 slides along the arcuate guide 106 when the inlet valve assembly 114 is coupled to the grip 42.

The wall portion 146 includes a cutout 150 in fluid communication with the channel 94 such that a bottom side of the apertures 142 are in fluid communication with the channel 94. A top side of the apertures 142 are in fluid communication with the central chamber 102. In the illustrated embodiment, the inlet valve 122 includes a stem 154 that is at least partially received within the hub 130 formed in the seat 118. In other words, the inlet valve 122 is seated upon and coupled to the hub 130 such that the inlet valve 122 at least partially covers the plurality of apertures 142.

With reference to FIG. 5, the inlet valve 112 is a one-way airflow valve in fluid communication with the central chamber 102 and the facemask 14. As explained in further detail herein, the inlet valve 122 permits airflow to the facemask 14 when a subject inhales and blocks airflow from the facemask 14 when a subject exhales. In the illustrated embodiment, the inlet valve 122 is an umbrella valve. In other embodiments, any suitable type of one-way inlet valve can be utilized. In the illustrated embodiment, the inlet valve 122 is elastomeric and has a default, neutral position where a skirt portion 158 is positioned flat and covers the apertures 142. The inlet valve 122 is configured to at least partially deflect away from the apertures 142 in response to a pressure differential across the inlet valve 122, thereby permitting airflow in one direction (inhale) but not the opposite direction (exhale). In other words, the skirt 158 deflects to open the apertures 142 in response to a subject inhaling through the device 10, and the skirt 158 returns to the undeflected position to close the apertures 142 in response to a subject exhaling through the device 10.

Figure 4A:
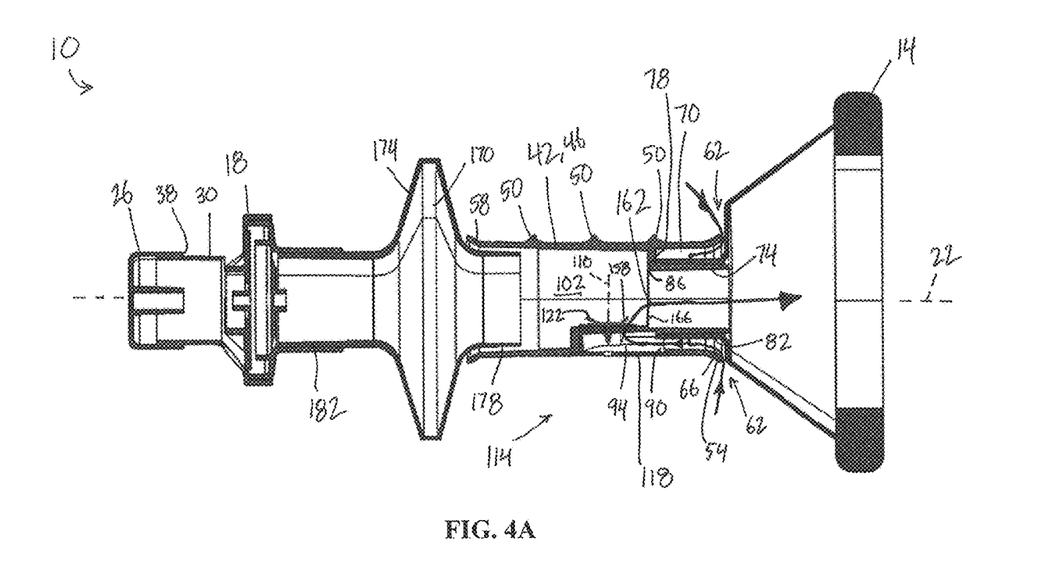
FIG. 4A is a cross-sectional view of the device of FIG. 1, illustrating an inhale airflow path.

As such, a first airflow path 162 (i.e., an inhale airflow path) (FIG. 4A) is defined from the air inlet 62, to the cavity 70, through the channel 94, through the inlet valve 122, into the central chamber 102, and to the facemask 14. In other words, the first airflow path 162 is defined through the inlet valve 122 when the device 10 is in a first configuration (i.e., an inhale configuration). In some embodiments, a filter is positioned along the first airflow path 162. For example, in some embodiments, a filter is positioned along a plane 166 (FIG. 4A). In some embodiments, the filter is microbial or a viral filter. As such, the device 10 allows free-flowing inhalation along the first airflow path 162 and a microbial filter to minimize aerosolization.

Figure 4B:
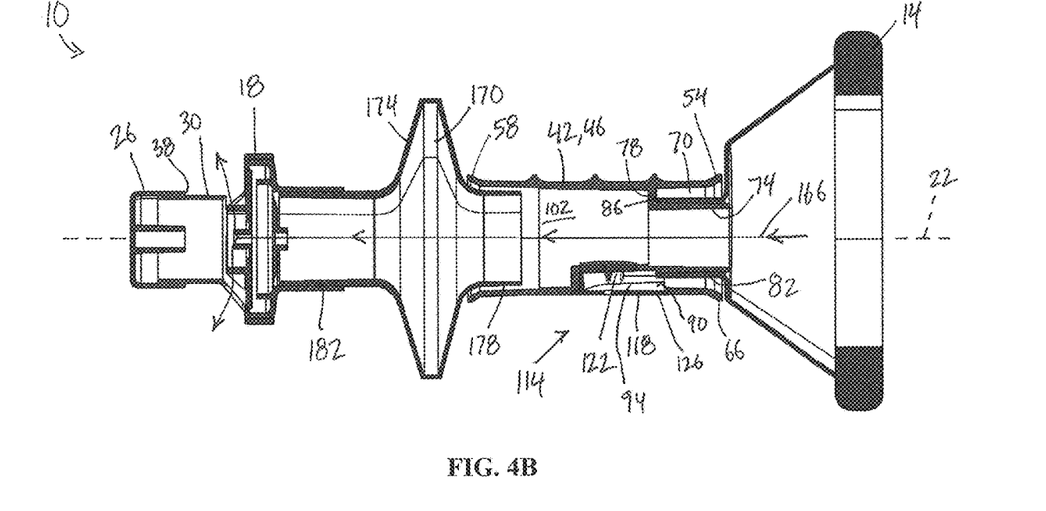
FIG. 4B is a cross-sectional view of the device of FIG. 1, illustrating an exhale airflow path.

With reference to FIG. 4B, in the illustrated embodiment, the device 10 includes a filter 170 that is positioned between the grip 42 and the outlet valve 18. In the illustrated embodiment, the filter 170 is positioned within a filter housing 174 with a first end 178 coupled to the second end 58 of the grip 42 and a second end 182 coupled to the outlet valve 18. In other words, the grip 42, the filter 170, and the outlet valve 18 are fluidly connected in series. In some embodiments, the filter 170 is a microbial or a viral filter. In some embodiments, the filter 170 is replaceable. The filter 170 reduces aerosolized microbes in the air, as well as protects the outflow valve 18 from contamination. The filter 170 is advantageous for use with patients with COVID-19, for example, or other PEEP responsive communicative diseases.

In other embodiments, the first end 54 or the second end 58 of the grip 42 are fluidly coupled to any suitable modular component (e.g., airflow filters, nebulizer ports, oxygen sources, etc.). In some embodiments, an oxygen delivery device is fluidly coupled to the air inlet 62. In other words, the air inlet 62 includes an attachment for oxygen delivery. In other embodiments, oxygen flows directly into the facemask 14.

As such, a second airflow path 166 (i.e., an exhale airflow path) (FIG. 4B) is defined from the facemask 14, through the central chamber 102 in the grip 42, through the filter 170, and out the outlet valve 18. In other words, the second airflow path 166 is defined through the outlet valve 18, but not through the inlet valve 122) when the device 10 is in a second configuration (i.e., an exhale configuration).

In operation, in a first configuration (i.e., an inhale configuration) air flows from the air inlet 62 to the facemask 14 and the subject's nose and mouth along the first airflow path 162. In other words, as the subject inhales with the facemask 14 pressed to their face, the inlet valve 122 deflects and places the facemask 14 in fluid communication with the air inlet 62. In a second configuration (i.e., an exhale configuration) air flows from the facemask 14 to the outlet valve 18 along the second airflow path 166 while the inlet valve 122 blocks the apertures 142. Flow along the second airflow path 166 is limited by the outlet valve 18 to create a positive pressure within the device 10. As such, the first airflow path 162 is air flowing to the facemask 14 and the second airflow path 166 is air flowing from the facemask 14.

The first airflow path 162 is not blocked by a user when the user holds the device 10 at the grip 42. Specifically, the inlet valve 122 is positioned within the grip 42 and shrouded by the seat 118 such that a user cannot obstruct the inlet valve 122. Likewise, the air inlet 62 is axially positioned between the grip 42 and the facemask 14 with 360 degrees of access such that a user's hand cannot block the air inlet 62. In other words, potential blocking of the first airflow path 162 is prevented by positioning the inlet valve 122 within the grip 42 and forming the air inlet 62 at the first axial end 54 of the grip 42.

Figure 6A:
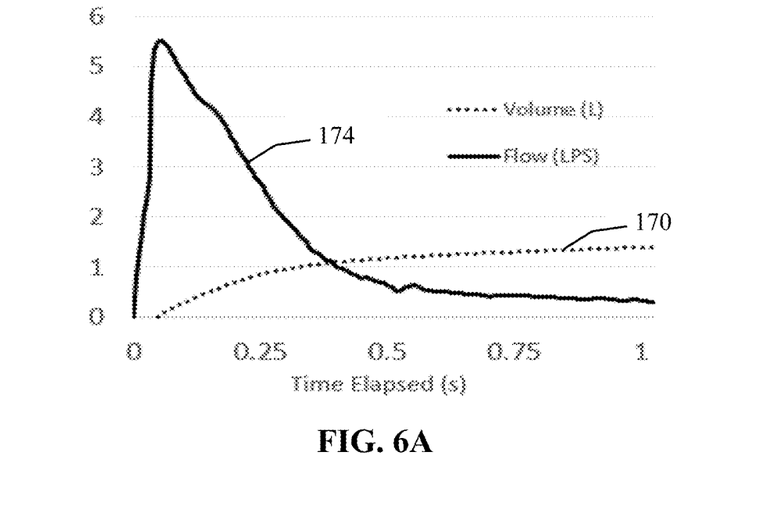
FIG. 6A is a graph illustrating an exhale volume (in L) and a flow (in L/sec) as a function of time for an example exhale through the device of FIG. 1.

With reference to FIG. 6A, an exhale volume 170 (in L) and a flow 174 (in L/sec) are shown as a function of time for an example exhale through the device 10. In other words, the volume of air exhaled by a user during an exhale is illustrated by the exhale volume 170, and the flow of that exhale is illustrated by the flow 174. In the illustrated example, the exhale volume 170 increases as a function of time, and the flow 174 initially spikes quickly but then decreases slower over time.

Figure 6B:
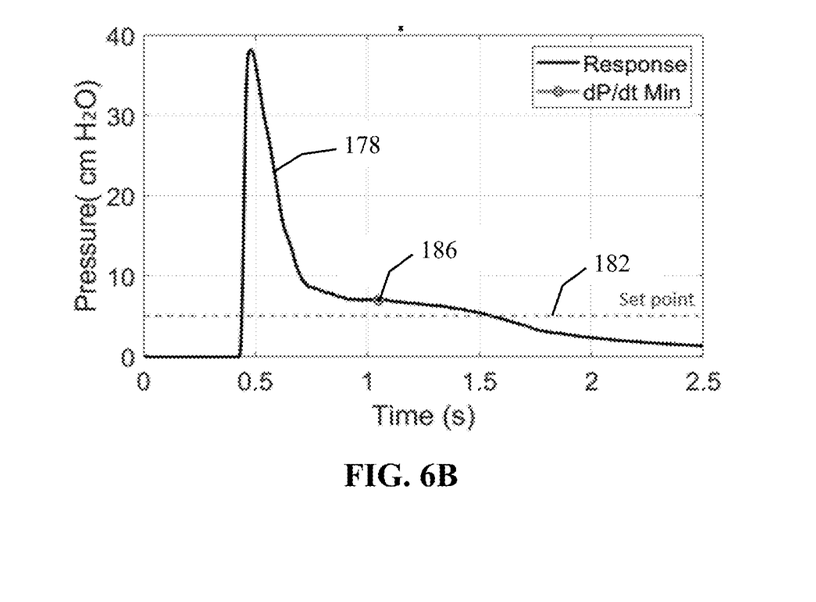
FIG. 6B is a graph illustrating a pressure (in cm $H_2O$) and a pressure threshold setpoint of an output valve shown as a function of time for an example exhale through the device of FIG. 1.

With reference to FIG. 6B, a pressure 178 (in cm $H_2O$) and a pressure threshold setpoint 182 of the output valve 18 are shown as a function of time for an example exhale through the device 10. In the illustrated example, the pressure threshold setpoint 182 is set to approximately 5 cm $H_2O$. As mentioned herein, the output valve 18 is adjustable and the pressure threshold setpoint can be adjusted by a user without the use of tools in a discrete (i.e., step-wise) or continuous manner. In other words, the outflow valve 18 is adjustable to provide prescribed expiratory resistance based on an individual patients' needs. The output valve 18 creates a transient pressure response (see pressure 178). When a patient exhales through the device 10, there is an initial spike of pressure followed by a transient plateau around the pressure threshold setpoint 182. In some embodiments, the initial spike in pressure is followed by an approximately 1-2 second long transient plateau dictated by the adjustable output valve 18. In the illustrated example, a point 186 of a minimum change in pressure (i.e., minimum dP/dt) occurs at time=1.05 seconds and pressure=6.94 cm $H_2O$.

Advantageously, the device 10 is an accessible, single user device with a low barrier for training and adoption. In other words, the device 10 is intuitive for a user to grasp, hold against their face, and operate. In addition, the device 10 is easily decontaminated. For example, the output valve 18 can be removed and either cleaned or replaced. Likewise, the facemask 14, filter 170, and the grip 42 can all be separated. Also, the device 10 can be wiped down or be cleaned with a soap and water cleaning protocol. The device 10 described herein is used for treating hypoxia and preventing progression to acute respiratory distress syndrome (ARDS).

Figure 7:
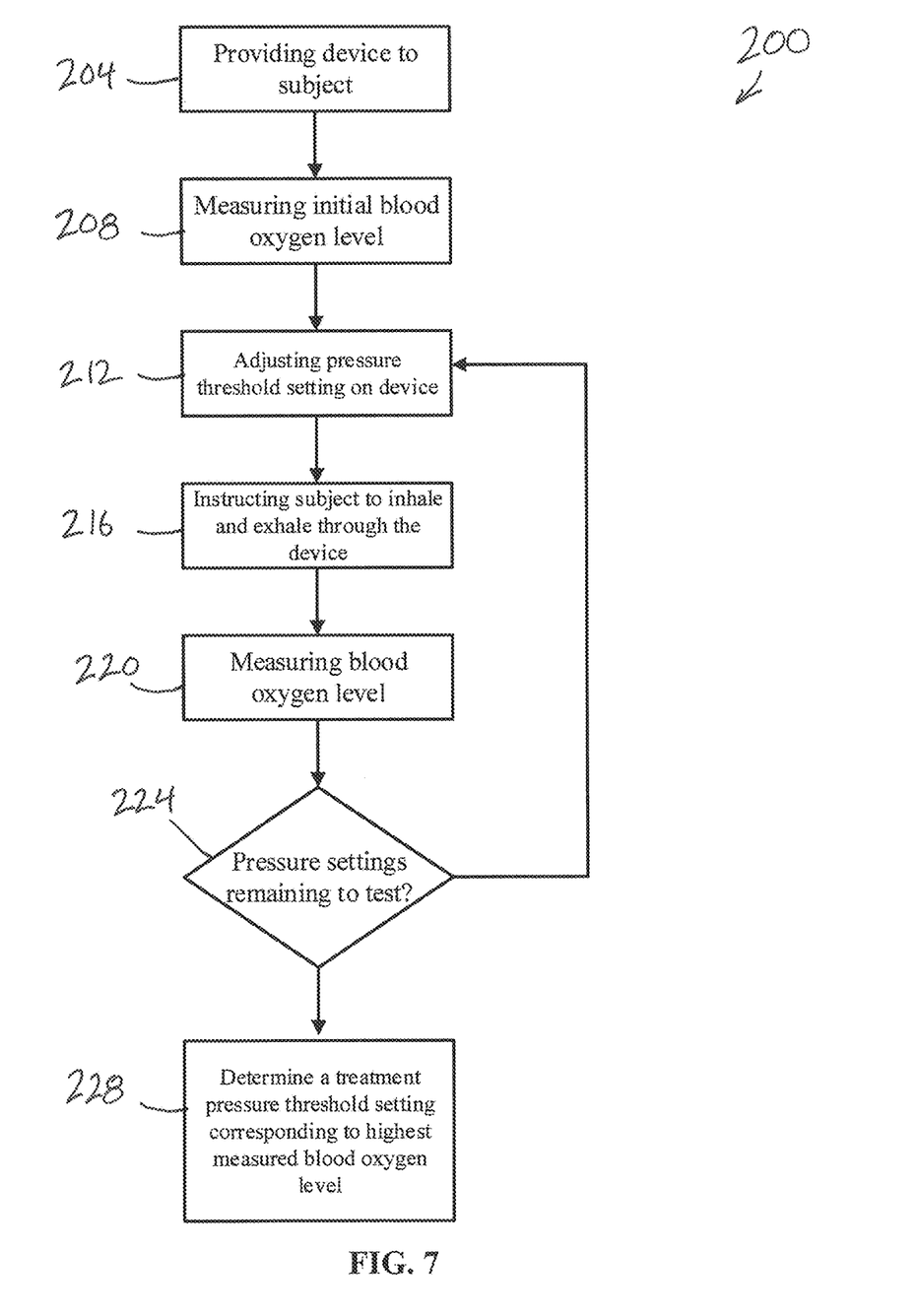
FIG. 7 is a flow diagram of a method for treating hypoxia in a subject.

With reference to FIG. 7, a method 200 of treating hypoxia in a subject is illustrated. In some embodiments, the method 200 of treating hypoxia in a subject includes the device 12. The method 200 includes providing the device 10, which includes the outlet valve 18, to a subject (STEP 204). The method 200 also includes measuring a first blood oxygen saturation level ($SpO_2$) of the subject (STEP 208) (i.e., measuring an initial oxygen level). In other words, the initial oxygen saturation level provides a baseline measurement at atmospheric pressure.

After the initial oxygen saturation level of the subject is measured, the device 10 is set at the lowest pressure threshold setting (e.g., 5 cm $H_2O$) (e.g., "a first pressure threshold"), the subject is instructed to firmly press the facemask 14 around their nose and mouth. In some embodiments, the subject is in a seated position. In other words, the method 200 includes a STEP 212 of adjusting the pressure threshold setting on the device 10 and a STEP 216 of instructing the subject to inhale and exhale through the device 10. In some embodiments, the pressure threshold of the device 10 is adjusted by aligning the indicia 34 with the bottom 38 of the knob 26. In some embodiments, the STEP 216 includes instructing the subject to inhale through the device 10 by taking a deeper breath than normal, and then steadily exhale into the device 10 until all their breath is out. The method 200 further includes a STEP 220 of measuring the oxygen saturation level of the subject after the subject has breathed through the device 10 (e.g., "a second oxygen saturation").

With continued reference to FIG. 7, the method 200 further includes a STEP 224 of determining whether any pressure settings of the device 10 remain to test on the subject (i.e., have all the pressure settings been tested yet). If there are pressure threshold settings remaining to test, the method 200 returns to STEP 212 and repeats STEP 212, STEP 216, and STEP 220. In other words, the method 200 includes adjusting the outlet valve 18 to a second setting corresponding to a second pressure threshold (e.g., 10 cm $H_2O$). In some embodiments, the second pressure threshold is larger than the first pressure threshold. Again, at the STEP 216 the subject is instructed to inhale and exhale through the device 10, followed by the STEP 220 of measuring an oxygen saturation level of the subject (e.g., a third oxygen saturation). In some embodiments, the method 200 includes waiting at least 30 seconds between measurements of the oxygen saturation of the subject (STEP 220). In other words, the method 200 includes instructing the subject to exhale fully between breaths and then breathe normally for at least 30 seconds between each trial of the mask. In some embodiments, the waiting between measurements is at least 2 minutes. In some embodiments, the waiting between measurements is for approximately 3 to 5 minutes. In some embodiments, the waiting between measurements is at least 4 minutes. If there are no pressure threshold setting remaining to test, the method 200 proceeds to STEP 228. In some embodiments, there are at least three pressure threshold settings for testing. In other embodiments, there are at least five pressure threshold settings (e.g., 5, 10, 15, 20 cm $H_2O$) for testing (i.e., measuring an oxygen saturation resulting form each pressure threshold setting).

With continued reference to FIG. 7, the STEP 228 includes determining a peak oxygen saturation, wherein the peak oxygen saturation is the largest of oxygen levels measured during the method 200. For example, when two different pressure threshold settings are tested, the comparison is made between the initial oxygen saturation (a first oxygen saturation), the second oxygen saturation (measured after using the device 10 at the first pressure threshold setting), and the third oxygen saturation (measured after using the device 10 at the second pressure threshold setting). The STEP 228 further includes determining a treatment pressure setting of the output valve 18 that corresponds to the peak oxygen saturation measured and adjusting the output valve 18 to the corresponding treatment setting. In other words, after testing each pressure threshold level of the outlet valve 18, the outlet valve 18 is set to the pressure threshold level that corresponds with achieving the highest oxygen level saturation measured during the method 200. In some embodiments, if two or more pressure threshold settings resulted in the equally high oxygen saturation measurement, the method 200 utilizes the lower of the settings. In some embodiments, if the highest oxygen saturation measurement is at the first valve (corresponding to atmospheric pressure), then the device 10 is set to its lowest pressure threshold setting.

Upon completion of the method 200, the device 10 is configured for continued use by a subject. In some embodiments, the subject has been diagnosed with COVID-19, forms of pneumonia, or lung injury. In some embodiments, the method 200 further includes decontaminating the device 10 by any one of: removing and replacing the outlet valve 18, the facemask 14, the filter 170, and wiping down the device 10 (e.g., with soap and water). In some embodiments, the method for treating hypoxia in a subject includes any combination of the steps described herein, in various orders. In some embodiments, steps may be omitted. Further, the order of the steps may be reversed, altered, or performed simultaneously.

The device 10 and the method 200 are used to improve oxygenation in patients with hypoxia (i.e., oxygen saturation less than approximately 94% on room air or requiring supplemental oxygen at baseline) by decreasing respiratory muscle work of breathing, decreasing atelectasis and improving functional residual capacity.

One skilled in the art will readily appreciate that the present disclosure is well adapted to carry out the objects and obtain the ends and advantages mentioned, as well as those inherent herein. The present disclosure described herein are exemplary embodiments and are not intended as limitations on the scope of the present disclosure. Changes therein and other uses will occur to those skilled in the art which are encompassed within the spirit of the present disclosure as defined by the scope of the claims.

Various features and advantages are set forth in the following claims.

What is claimed is:

1. A device comprising:
  a facemask;
  an outlet valve in fluid communication with the facemask;
  a grip positioned between the facemask and the outlet valve; and
  an inlet valve in fluid communication with the facemask, wherein the inlet valve is positioned within the grip; and
  wherein an air inlet is formed between the grip and the facemask.

2. The device of claim 1, wherein a first airflow path is defined through the inlet valve when the device is in a first configuration, and wherein a second airflow path is defined through the outlet valve when the device is in a second configuration.

3. The device of claim 2, wherein the first airflow path is to the facemask and wherein the second airflow path is from the facemask.

4. The device of claim 1, wherein the air inlet is an opening positioned between an axial end of the grip and the facemask.

5. The device of claim 4, wherein the opening circumferentially extends 360 degrees.

6. The device of claim 4, wherein a cavity formed in the grip is in fluid communication with the opening.

7. The device of claim 1, wherein an oxygen delivery device is fluidly coupled to the air inlet.

8. The device of claim 1, further comprising a seat coupled to the grip, wherein the inlet valve is coupled to the seat.

9. The device of claim 8, wherein the seat is in fluid communication with an air inlet formed between the grip and the facemask, and wherein the seat includes an aperture at least partially covered by the inlet valve.

10. The device of claim 9, wherein the inlet valve is an umbrella valve with a stem at least partially received within a hub formed in the seat.

11. The device of claim 1, wherein the outlet valve is a positive end expiration pressure valve.

12. The device of claim 1, further comprising a filter in fluid communication with the facemask.

13. The device of claim 12, wherein the filter is positioned within a filter housing with a first end coupled to the grip and a second end coupled to the outlet valve.

14. A device comprising:
  a facemask;

an outlet valve in fluid communication with the facemask;
a grip positioned between the facemask and the outlet valve;
an inlet valve in fluid communication with the facemask, wherein the inlet valve is positioned within the grip;
a seat coupled to the grip, wherein the inlet valve is coupled to the seat; and
wherein the seat is in fluid communication with an air inlet formed between the grip and the facemask, and wherein the seat includes an aperture at least partially covered by the inlet valve.

15. The device of claim 14, wherein the inlet valve is an umbrella valve with a stem at least partially received within a hub formed in the seat.

16. The device of claim 14, wherein a first airflow path is defined through the inlet valve when the device is in a first configuration, and wherein a second airflow path is defined through the outlet valve when the device is in a second configuration, and wherein the first airflow path is to the facemask and wherein the second airflow path is from the facemask.

17. The device of claim 14, further comprising a filter in fluid communication with the facemask; wherein the filter is positioned within a filter housing with a first end coupled to the grip and a second end coupled to the outlet valve.

18. A device comprising:
a facemask;
an outlet valve in fluid communication with the facemask;
a grip positioned between the facemask and the outlet valve; and
an inlet valve in fluid communication with the facemask, wherein the inlet valve is positioned within the grip;
a filter in fluid communication with the facemask; wherein the filter is positioned within a filter housing with a first end coupled to the grip and a second end coupled to the outlet valve.

19. The device of claim 18, further comprising a seat coupled to the grip, wherein the inlet valve is coupled to the seat, and wherein the seat is in fluid communication with an air inlet formed between the grip and the facemask, and wherein the seat includes an aperture at least partially covered by the inlet valve.

20. The device of claim 18, wherein a first airflow path is defined through the inlet valve when the device is in a first configuration, and wherein a second airflow path is defined through the outlet valve when the device is in a second configuration, and wherein the first airflow path is to the facemask and wherein the second airflow path is from the facemask.

* * * * *